US009738663B2

(12) United States Patent
Nonnenmacher et al.

(10) Patent No.: US 9,738,663 B2
(45) Date of Patent: Aug. 22, 2017

(54) PROCESS FOR THE PREPARATION OF AMINOARYL- AND AMINOHETEROARYL BORONIC ACIDS AND ESTERS

(71) Applicant: EUTICALS S.P.A., Milan (IT)

(72) Inventors: Michael Nonnenmacher, Leimen (DE); Torsten Busch, Frankfurt am Main (DE)

(73) Assignee: EUTICALS S.P.A. (IT)

( * ) Notice: Subject to any disclaimer, the term of this patent is extended or adjusted under 35 U.S.C. 154(b) by 0 days.

(21) Appl. No.: 14/888,844

(22) PCT Filed: Apr. 30, 2014

(86) PCT No.: PCT/EP2014/058873
§ 371 (c)(1),
(2) Date: Nov. 3, 2015

(87) PCT Pub. No.: WO2014/180735
PCT Pub. Date: Nov. 13, 2014

(65) Prior Publication Data
US 2016/0075723 A1 Mar. 17, 2016

(30) Foreign Application Priority Data
May 6, 2013 (EP) .................... 13425068

(51) Int. Cl.
C07F 5/04 (2006.01)
C07F 5/02 (2006.01)

(52) U.S. Cl.
CPC .............. *C07F 5/025* (2013.01); *C07F 5/04* (2013.01)

(58) Field of Classification Search
CPC ..................... C07F 5/04; C07F 5/02
USPC ..................... 558/288, 298; 546/13
See application file for complete search history.

(56) References Cited

U.S. PATENT DOCUMENTS 7,196,219 B2   3/2007 Scherer et al.
2008/0269523 A1 10/2008 Kressierer et al.

FOREIGN PATENT DOCUMENTS

| CN | 102387260 A | 3/2012 |
| CN | 103524542 A | 1/2014 |
| DE | 102007020401 A1 | 11/2008 |
| WO | 2010100127 A1 | 9/2010 |

OTHER PUBLICATIONS

Heaney, H. et al., "Lanthanide Triflate Catalysed Reactions of Acetals with Primary Amines and Cascade Cyclisation Reactions," Synlett, No. 6, 1998, pp. 640-642.

Yeoul, L.B. et al., "Bimatallicl anilido-aldimine zinc complexes for epoxide/CO2 copolymerization," Journal of the American Chemical Society, ACS Publications, US, vol. 127, No. 9, Mar. 9, 2005.
PCT International Search Report dated Jul. 28, 2014 for Intl. App. No. PCT/EP2014/058873, from which the instant application is based, 5 pgs.
European Search Report dated Oct. 13, 2013 for related European Application No. 13425068, 8 pgs.
Brown, H.C. et al., A Simple Preparation of Boronic Esters from Organolithium Reagents and Selected Trialkoxyboranes, Organometallics 1983, 2, 1316-1319.
Booth, C.J. et al., "Novel Chiral Liquid Crystals Derived from (R)-2(4-Hydroxyphenolxy)propan-1-ol," J. Mater. Chem., 1993, 3(8), 821-832.
Miyara, N. et al., "The Palladium-Catalyzed Cross-Coupling Reaction of Phenylboronic Acid with Haloarenes in the Presence of Bases," Synthetic Communications, 1981, 11(7), 513-519.
Godard, A. et al., "Convergent Synthesis of Streptonigrin and Lavendamycin Analogues," Tetrahedron Letters, 1993, vol. 34, No. 9, 7919-7922.
Seaman W. et al., "Derivatives of Phenylboric Acid, Their Preparation and Action upon Bacteria," Feb. 9, 1931, Contribution from the Baker Laboratory of Chemistry at Cornell University, 711-723.

(Continued)

Primary Examiner — Charanjit Aulakh
(74) Attorney, Agent, or Firm — Fredrikson & Byron, P.A.

(57) ABSTRACT

The present invention relates to a process for the preparation of aminoaryl- and aminoheteroaryl boronic acids and esters thereof of formula (I) in high yield. The claimed process uses diarylketal formula (V) to generate an arylbromide of formula (III) in which the amino-group is protected as bisarylmethylidenimino-group, which is then transformed into a formula (I) compound.

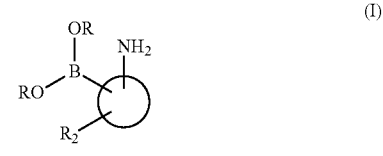

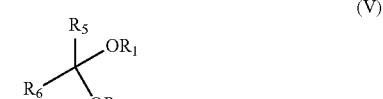

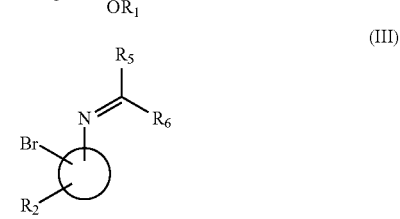

21 Claims, No Drawings

(56) References Cited

OTHER PUBLICATIONS

Lerrmann, T. et al., "Highly Efficient One-Pot Access to Functionalized Arylboronic Acids via Noncryogenic Bromine/Magnesium Exchanges," Organic Letters, 2011, vol. 13, No. 17, 4479-4481.
Wallow, T. et al., "In Aqua Synthesis of Water-Soluble Polyp-phenylene) Derivatives," J. Am. Chem. Soc. 1991, 113, 7411-7412.
Oh-E, Tet al., "Paladium-Catalyzed Cross-Coupling Reaction of Organoboron Compounds with Organic Triflates," J. Org. Chem. 1993, 58, 2201-2208.
Das, S. et al., "Synthesis and crystal structure of 4-amino-3-fluorophenylboronic acid," Tetrahedron Letters 44, 2003, 7719-7732.
Beley et al., "Synthesis of Bis-cyclometallating N—C—N Hexadentate Ligands via C—C Aromatic Couplings and their Dinuclear Ruthenium(II) Complexes," Tetrahedron Letters, vol. 34, No. 18, Apr. 30, 1993, pp. 2933-2936.

PROCESS FOR THE PREPARATION OF AMINOARYL- AND AMINOHETEROARYL BORONIC ACIDS AND ESTERS

RELATED APPLICATIONS

This application is a 35 U.S.C. 371 national stage filing from International Application No. PCT/EP2014/058873, filed Apr. 30, 2014, which claims priority to European Application No. 13425068.7, filed May 6, 2013, the teachings of which are incorporated herein by reference.

The present invention relates to a process for the preparation of aminoaryl- and aminoheteroaryl boronic acids and esters thereof of formula (I) in high yields

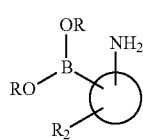

starting from a dialkyl ketal derivative of formula (V)

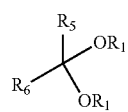

BACKGROUND OF THE INVENTION

Boronic acid derivatives are widely used in organic synthesis for the formation of carbon-carbon bonds. In Suzuki coupling, an aryl halide and an aryl- or vinyl-borate ester or boronic acid are coupled using $Pd(PPh_3)_4$ (N. Miyaura, T. Yanagi and A. Suzuki Synth. Commun. 1981, 11, 513). Aryl triflates are also effective coupling partners (T. Ohe, N. Miyaura and A. Suzuki J. Org. Chem. 1993, 58, 2201).

Boronic acid derivatives have been used during natural product synthesis (P. Rocca et al. Tetrahedron Lett. 1993, 34, 7919), material synthesis (J. P. Sauvage et al. Tetrahedron Lett. 1993, 34, 5125), poly(arylene) polymerization (T. I. Wallow et al. J. Am. Chem. Soc. 1991, 113, 7411) and oligoarene liquid crystals preparation (J. W. Goodby et al. J. Mater. Chem. 1993, 3, 821). One important feature of this kind of chemistry is that boronic acids, in general, are relatively non-toxic and air- and moisture-stable compounds.

Organic aryl, heteroaryl boronic acids and their derivatives can be obtained by different synthetic routes: cross-coupling of bis(pinacolato)diboron ($B_2pin_2$) with aryl halides and vinyl halides (Miyaura borylation reaction) or by conversion of aryllithium or arylmagnesium compounds with a boronic acid trialkyl ester followed by acid hydrolysis (T. Leermann, F. R. Leroux, F. Colobert Org. Lett. 2011, 13, 4479-4481).

However, the above described synthetic approaches for the preparation of organic aryl and heteroaryl boronic acids present some limitations, mainly linked to the presence of some functional groups that are not compatible with the employed reaction conditions. For example, the presence of an amino group can interfere with the formation of the organometallic compound. Several synthetic strategies were thus applied for the preparation of aminoaryl- and aminoheteroaryl boronic acids and esters using different amino protective groups.

US patent application 2008/269523A1 describes the possibility to protect bromo aminoaryl and bromo aminoheteroaryl substrates as imino derivatives with benzophenone.

Alternatively, CN102367260A describes the possibility to use t-butyloxycarbonyl derivatives (t-BOC derivatives) of bromo aminoheteroaryl compounds.

Moreover, the amino group can also be protected as N,N-dibenzyl derivative, which is a functional group that can be removed by catalytic hydrogenation (see U.S. Pat. No. 7,196,219B2) or as N,N-trimethylsilyl derivative, which is unstable to moisture (Tetrahedron Lett. 2003, 44(42), 7719-7722).

Unfortunately, the scale-up of these aforementioned synthetic approaches have some important drawbacks, since upon working on the scale of kilograms, it has never been possible to obtain the described overall yields of US2008/269523A1 (i.e. 38-66%), but only considerable lower yields (about 2-10%) in very long reaction times (several days) in order to obtain a conversion higher than 90%.

The main problem connected with the lack of reproducibility of what described in US2008/269523A1 is due to the formation of the imino derivatives; as a matter of fact, the reaction between benzophenone and the aminoaryl or aminoheteroaryl derivative described in Examples 1-10 of the above patent application occurs with very low yields.

Other parameters have been taken into consideration to solve this problem, such as the presence of water, the employed catalyst and the solvent. In particular, the presence of water is known to be critical for the preparation of imino derivatives, since it can influence negatively the equilibrium of the reaction.

The longer reaction times at larger scale can also explain the lower/varying yields because the application of harsh reaction conditions for long periods of time can clearly results in degradation.

Although the reason for this unexpected behavior is not completely clear, it was required to improve the method described in US2008/0269523A1 in order to get to reasonable reaction rate at larger scale (kg or mt) without sacrificing the benefits of the method described.

Lastly, di-tert-butylcarbonate, the protective reagent described in CN102367260A, is known to be very toxic (fatal if inhaled), flammable and unstable to moisture, which makes it particularly unsuitable for industrial use.

It is therefore desirable to provide an improved process for preparing aminoaryl- and aminoheteroaryl boronic acids in high yields on a large scale, which makes use of non-toxic and easy-to-handle reagents.

DESCRIPTION

It has now been surprisingly found a new synthetic approach for the preparation of imino derivatives of bromo aminoaryl or bromo aminoheteroaryl compounds, affording the corresponding boronic acids and esters in high yields.

The process of the present invention is disclosed in the following scheme.

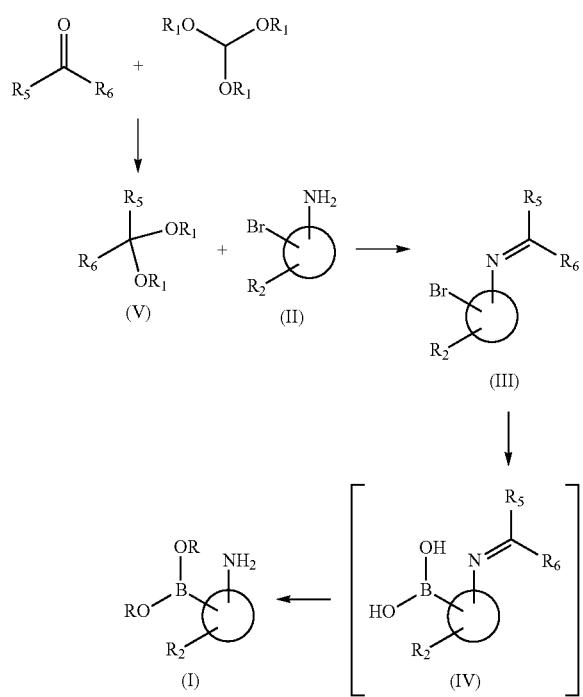

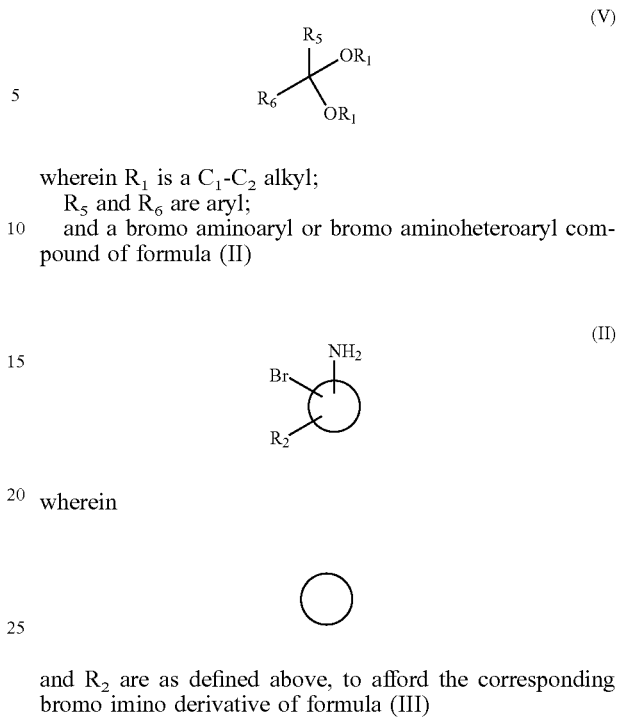

wherein $R_1$ is a $C_1$-$C_2$ alkyl;
$R_5$ and $R_6$ are aryl;
and a bromo aminoaryl or bromo aminoheteroaryl compound of formula (II)

wherein and $R_2$ are as defined above, to afford the corresponding bromo imino derivative of formula (III)

wherein $R_2$, $R_5$ and $R_6$ are as defined above.

As used herein, the term "$C_1$-$C_3$ alkyl" means linear or branched chain alkyl groups having from 1 to 3 carbon atoms and includes n- and isopropyl, ethyl and methyl.

The term "$C_1$-$C_2$ alkyl" means alkyl groups having from 1 to 2 carbon atoms and includes ethyl and methyl.

The term "aryl" according to the present invention refers to aromatic mono- and polycarbocyclic ring systems, wherein the individual carbocyclic rings in the polyring systems may be fused or attached to each other via a single bond. Suitable aryl groups include, but are not limited to, phenyl, naphthyl and biphenyl. The term "heteroaryl" according to the present invention refers to a 4- to 8-membered monocyclic ring, which consists of carbon atoms and one or more heteroatoms selected from N, O and S. Suitable heteroaryl groups include, but are not limited to, pyridine, pyrazine, imidazole, pyrazole, pyran, triazole.

The dialkyl ketal derivative of formula (V) can be obtained according to methods well known in the art, such as for example the method described in Greene T. W. et al. Protecting groups in Organic synthesis, Wiley, Third Edition.

An object of the present invention is therefore a process for the preparation of aminoaryl- and aminoheteroaryl boronic acids and esters thereof of Formula (I), wherein

represents an aryl or heteroaryl group;

$R_2$ is selected from H, Cl, F, $C_1$-$C_3$ alkyl and $C_1$-$C_3$ alkoxy; preferably $R_2$ is H.

R is selected from H, $C_1$-$C_2$ alkyl or, taken together with the other R, forms a ring of formula

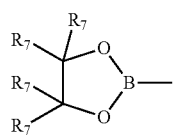

wherein $R_7$ is H or $C_1$-$C_3$ alkyl

Said process comprises a condensation reaction between a dialkyl ketal derivative of formula (V)

Typically, dialkyl ketal derivatives are obtained by reacting a ketone of formula $R_5R_6C=O$ with a trialkyl orthoformate of formula $HC(OR_1)_3$, optionally in the presence of an acid catalyst, wherein $R_1$, $R_5$ and $R_6$ are as defined above.

According to an embodiment of the present invention, a ketone, preferably benzophenone in a concentration comprised between 1.5 mol/l and 3.5 mol/l, preferably of about 2.5 mol/l is reacted with a trialkyl orthoformate, preferably trimethyl orthoformate or triethyl orthoformate in a molar ratio comprised between 1.0 and 2.0 with respect to said ketone, preferably in a molar ratio of 1.5 with respect to said ketone, optionally in the presence of an acid catalyst. Any acidic compound known to the skilled person can be used as acid catalyst. Examples of acid catalysts are sulfuric acid, hydrochloric acid, sulfonic acids, such as para toluene sulfonic acid monohydrate, para toluene sulfonic acid ferric salt, or an acidic ion exchange resin such as Serolit Red H⁺.

A preferred acid catalyst according to the present invention is para toluene sulfonic acid monohydrate.

According to the process of the present invention, this reaction can be performed in an organic solvent, preferably an alcoholic solvent of formula $R_1$—OH or in a mixture of solvents, at a temperature comprised between 40° C. and 150° C., preferably at reflux temperature, for a period of time comprised between 1 and 5 h.

The mixture of solvents used in the aforementioned reaction is preferably a mixture of an alcoholic solvent, more preferably an alcohol of formula $R_1$—OH, wherein $R_1$ is as defined above, and an organic solvent such as linear, cyclic or branched hydrocarbons, linear or cyclic (poly)ethers or esters, preferably toluene, 1,4-dioxane, diethyleneglycol dimethyl ether or xylenes.

According to a still more preferred embodiment of the present invention, this protection reaction takes place in a mixture of an alcoholic solvent of formula $R_1$—OH and toluene, in a volume ratio comprised between 3 and 2.

The dialkyl ketal derivative of formula (V) of the present invention can be isolated or can be used directly in the next step without any further purification. Preferably, said derivative is not isolated and after removal by distillation of potentially unreacted starting material and said alcoholic solvent, said dialkyl ketal derivative is condensed directly with the bromo aminoaryl or bromo aminoheteroaryl compound of formula (II).

According to the present invention, the molar ratio between said ketone and said bromo aminoaryl or bromo aminoheteroaryl compound of formula (II) is comprised between 0.75 and 2, preferably between 1 and 1.25.

According to an embodiment of the present invention, the condensation reaction is performed in an organic solvent, preferably an aprotic solvent selected from tetrahydrofuran, methyltetrahydrofuran, toluene, 1,4-dioxane, hexane, cyclohexane, heptane and/or mixtures thereof, at a temperature comprised between 70° C. and 140° C., preferably at 100-120° C.

According to a more preferred embodiment of the present invention, said condensation reaction is performed in toluene, still more preferably for a period of time comprised between 6 and 24 h, followed by partial removal through distillation of a volume comprised between 30% and 40% of the total volume of the reaction mixture.

The residue thus obtained can be isolated by using purification techniques well known to those skilled in the art, such as precipitation, crystallization and the like. Preferably, the imino derivative of formula (III) is isolated by crystallization in an alcoholic solvent or an aliphatic hydrocarbon solvent, more preferably in a $C_1$-$C_4$ alcanol or heptanes, hexane or methylcyclohexane, still more preferably methanol or heptane.

These new experimental conditions allow obtaining the imino derivative of formula (III) in high yields, thus making it possible to overcome the problems of scaling up of the process and low rate of conversion previously discussed.

Another object of the present invention is the use of a dialkyl ketal derivative of formula (V) as intermediate in the process of preparation of aminoaryl- and aminoheteroaryl boronic acids and esters.

Still another object of the present invention is the process for the preparation of aminoaryl- and aminoheteroaryl boronic acids and esters thereof of Formula (I), further comprising the metalation of the bromo imino derivative of formula (III) and conversion with a compound of formula $B(OR')_3$, wherein R' is a $C_1$-$C_3$ alkyl to afford the corresponding boronic acid derivative of formula (IV)

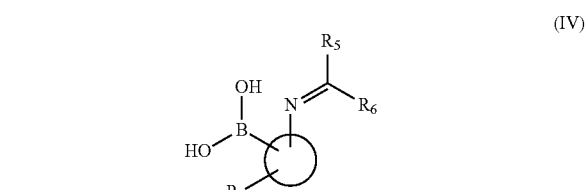

(IV)

wherein

, $R_2$, $R_5$ and $R_6$ are as defined above.

Bromo imino derivatives of formula (III) can be converted into the corresponding aminoaryl and aminoheteroaryl boronic acids and esters thereof using conventional methods reported in literature (see for instance, US2008/2369523; U.S. Pat. No. 7,196,219B2; Brown H. C., Cole T. E. Organometallics 1983, 2, 1316-1319; Seaman W. et al. J. Am. Chem. Soc. 1931, 53, 711-723).

According to the process of the present invention, the bromo imino derivative of formula (III) is dissolved in an aprotic organic solvent selected from saturated or unsaturated hydrocarbons, such as hexane, heptane, cyclohexane, toluene, linear or cyclic ethers such as tetrahydrofuran, methyl tetrahydrofuran, 1,4-dioxane, diethyl ether, diisopropyl ether and/or mixtures thereof.

A preferred solvent is a linear or cyclic ether, more preferably is tetrahydrofuran or methyl tetrahydrofuran optionally in mixture with a saturated or unsaturated hydrocarbon.

Suitable conditions for halogen-metal exchange can be obtained using organolithium compounds, preferably alkyl lithium compounds, more preferably n-butyl lithium or n-hexyl lithium at a temperature comprised between −50° C. and −100° C.

Said alkyl lithium compound is preferably used in a concentration comprised between 1.5 mol/l and 3.5 mol/l, preferably in a concentration of about 2.5 mol/l.

The reaction mixture is left to react at said temperature for a time comprised between 15 minutes and 4 hours, preferably between 30 minutes and 1 hour.

When full conversion is reached, a compound of formula B(OR')$_3$ wherein R' is a C$_1$-C$_6$ alkyl, preferably methyl, ethyl or isopropyl, more preferably isopropyl, is added to the reaction mixture in a molar ratio comprised between 1.0 and 1.5, with respect to the bromo imino derivative of formula (III).

According to a preferred embodiment of the present invention, during said addition, the temperature is maintained between −50° C. and −100° C. for a period of time comprised between 0.5 and 1.5 hours, affording the corresponding boronic acid of formula (IV).

In an alternative embodiment the reaction mixture containing compound III can be mixed with a compound of formula B(OR')$_3$ prior to addition of the lithium reagent. Upon addition of the lithium reagent at −50° C. to −100° C. the boronic acid of formula IV is generated directly in the reaction mixture.

Preferably, said compound of formula (IV) is not isolated and is subsequently subjected to acidic workup, in order to deprotect the imino group and to obtain the corresponding aminoaryl or aminoheteroaryl boronic acid of formula (Ia), in which R$_3$ and R$_4$ are both hydrogen, and

and R$_2$ are as defined above.

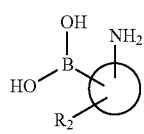

(Ia)

According to a preferred embodiment, said acidic workup takes place at a temperature comprised between −50° C. and 30° C., using a mineral acid such as hydrochloric or sulfuric acid.

The compound (Ia) can be isolated as free base or in a salified form depending on the pH of the reaction mixture, preferably in a salified form, more preferably in form of a hydrogen sulfate or hydrogen chloride salt.

It has to be pointed out that when isolating the compound (Ia) or the corresponding addition salts thereof it has also been possible to recover the starting ketone of formula R$_5$R$_6$C=O, as by-product of the above described reaction, which represents a further advantage of the process of the present invention.

If desired, the boronic acid derivative of formula (Ia) can be converted directly from the reaction mixture into the corresponding ester of formula (I), by esterification with an alcohol of formula R—OH, wherein R is as defined above.

Typically, the boronic ester of formula (I) is prepared by reaction of the boronic acid of formula (Ia), with an alcohol of formula R—OH, preferably pinacol, 1,2-ethanediol, and 1,4-butanediol at a pH comprised between 7.0 and 8.5.

Said alcohol is preferably used in a molar ratio comprised between 0.8 and 1.5, with respect to the bromo imino derivative of formula (III).

According to a preferred embodiment of the present invention, said boronic acid of formula (Ia) is dissolved in a biphasic aqueous/organic system, in which said organic solvent is selected from toluene, xylenes, C$_5$-C$_{10}$ linear or branched hydrocarbons, ethers and/or mixtures thereof, preferably is toluene.

The volume ratio between said aqueous solvent and said organic solvent is preferably comprised between 0.5 and 1.5, more preferably about 1.

The aminoaryl- or aminoheteroaryl boronic acid ester can be isolated by conventional purification techniques, such as precipitation, crystallization and the like, preferably is isolated by crystallization in an apolar solvent.

Examples of suitable apolar solvents are saturated or unsaturated hydrocarbons, such as hexane, heptane, cyclohexane, toluene, preferably heptane.

The following examples are intended to illustrate, but in no way to limit the scope of the invention.

EXAMPLES

Example A

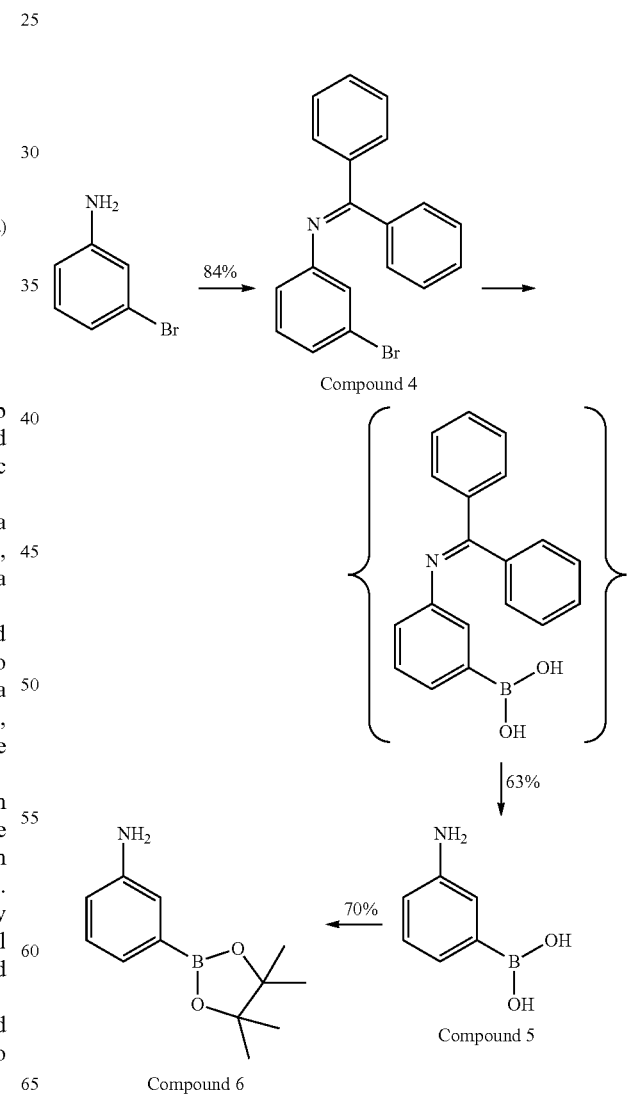

Preparation of 3-aminophenylboronic acid pinacol ester

Step 1—Preparation of 3-bromo-N-(diphenylmethylene)-Benzenamine (Compound 4) by Reaction with benzophenone dimethyl ketal Prepared "in situ" from benzophenone and trimethylorthoformate Formation of the Ketal:

100 kg of Benzophenone (550 Moles) are converted to the respective dimethyl ketal by treatment with 1.5 mole equivalents of trimethylorthoformate in a refluxing mixture of toluene and methanol (1:3, 5 L/kg benzophenone) under acid catalysis (5 mol % p-toluene sulfonic acid monohydrate). When the reaction is complete, solvents and access reagent are removed by distillation and replaced by toluene. To the resulting mixture, 1 mole equivalent of bromoaniline is added. The mixture is refluxed and partly concentrated until the conversion is complete (12 to 18 hours). Formed solids are removed by filtration and subsequently distillation is continued until the major part of the volatiles is removed. To the resulting concentrated solution/melt an equal amount of methanol is added and product crystallization is initiated by cooling. The resulting suspension is stirred for 30 min at 10° C. and subsequently the formed solid is collected by filtration. The solid is washed with methanol (0.5 L/kg benzophenone) and dried under vacuum to a constant weight at 25° C. 158 kg of compound 4 are obtained (470 moles; 86% molar yield on benzophenone).

Step 2—Preparation of 3-aminophenylboronic acid (Compound 5) from 3-bromo-N-(diphenylmethylene)-Benzenamine (Compound 3)

3-bromo-N-(diphenylmethylene)-Benzenamine (80.0 g; 0.24 Moles) is charged to a cryogenic reactor together with 1.4 eq of triisopropylborate and dissolved in tetrahydrofurane. The resulting solution is cooled to −80° C. under inert atmosphere and 1.35 eq of n-butyllithium is added as a solution in n-hexane maintaining the internal temperature. When full conversion is reached, the reaction mixture is added to a mixture of diluted sulphuric acid (1M) and toluene. The layers are split to obtain an aqueous solution of 3-aminophenylboronic acid hydrogen sulphate salt (Assay yield: 85%) (*point 1). 3-aminophenylboronic acid (compound 5) can be obtained by precipitation at the temperature of 0-5° C. from 0.5M aqueous solutions at pH 7.2 (pH correction with aqueous NaOH 33%). After filtration and drying under vacuum at 40° C. for 8 hours 21.7 g of compound 5 was obtained (0.16 Moles; 66% molar yield).

Step 3—Preparation of 3-aminophenylboronic acid pinacolate ester (2-(3-bromophenyl)-4,4,5,5-tetramethyl-1,3,2-Dioxaborolane; Compound 6) from 3-aminophenylboronic acid hydrogen sulphate Salt Solution of Example 2

1V of Toluene was added to 300 g of 3-aminophenylboronic acid hydrogen sulphate salt solution (obtained at *point 1 of the previous example and containing about 202 mmoles of product) and, under stirring, the pH value of this mixture was corrected to a final pH value of 8.0 with NaOH 33%. 1 eq. Of Pinacol was added and the obtained reaction mixture maintained under stirring at room temperature until the conversion was complete. The organic phase was separated and evaporated under vacuum to residue. 1V of Heptane was added and the obtained slurry maintained under stirring at 20-25° C. for 1 hour to afford a precipitate that was recovered by filtration and dried under vacuum (200 mmHg) at 40° C. for 8 hours to give 36.5 g of compound 6 (169 mmoles; 84% yields).

Overall molar yields from Benzophenone (without isolation of intermediate compound 5): 61%

Examples B-G

Using the same experimental conditions detailed in Example A (steps 1-3) also the compounds detailed in Examples B-H were prepared. The obtained yields are collected in Table 1.

TABLE 1

| % Molar yields of examples A-G | | | |
|---|---|---|---|
| Example | Step 1 | Step 2* | Step 3 |
| A | 86 | 66 | 84 |
| B | 82 | 60 | 80 |
| C | 80 | 59 | 78 |
| D | 89 | 65 | 75 |
| E | 75 | 62 | 50 |
| F | 85 | 65 | 73 |
| G | 78 | 62 | 75 |

*Note: yields on isolated compound

Example B

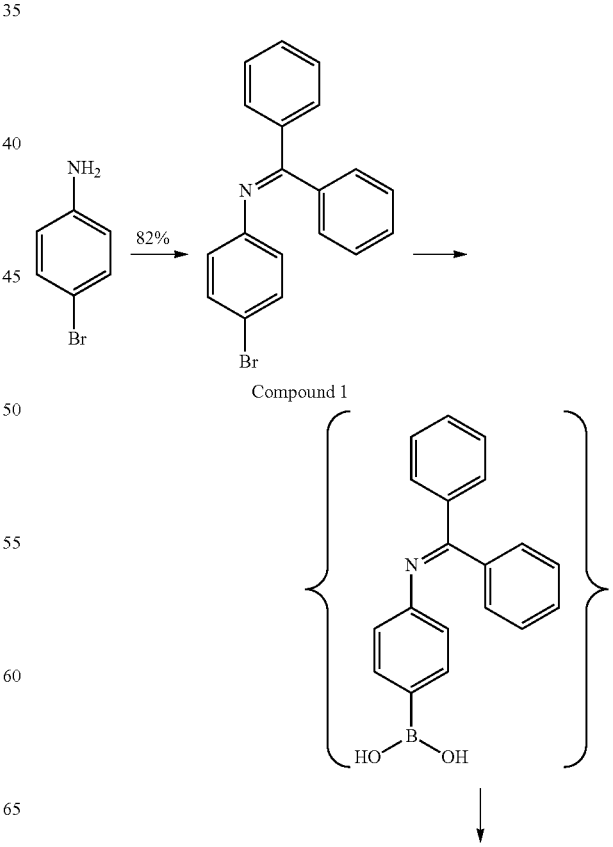

Compound 1

-continued
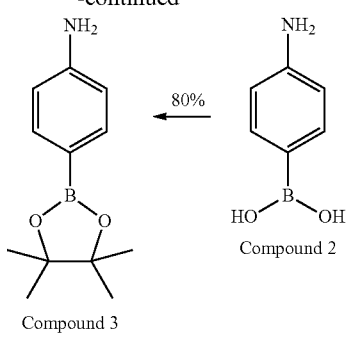
Preparation of 4-aminophenylboronic acid pinacol ester
Example C
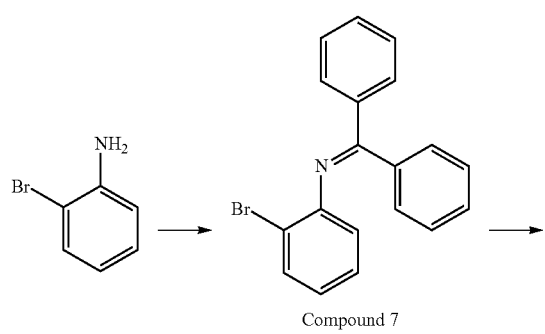
Preparation of 2-aminophenylboronic acid pinacol ester
Example D
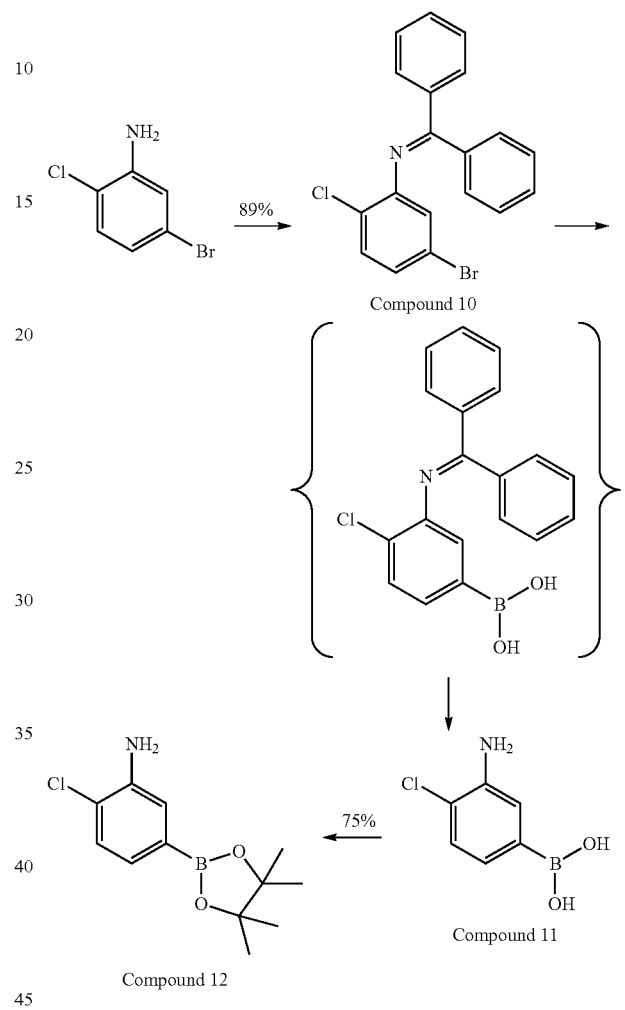
Preparation of 3-amino, 4-chlorophenylboronic acid pinacol ester
Example E
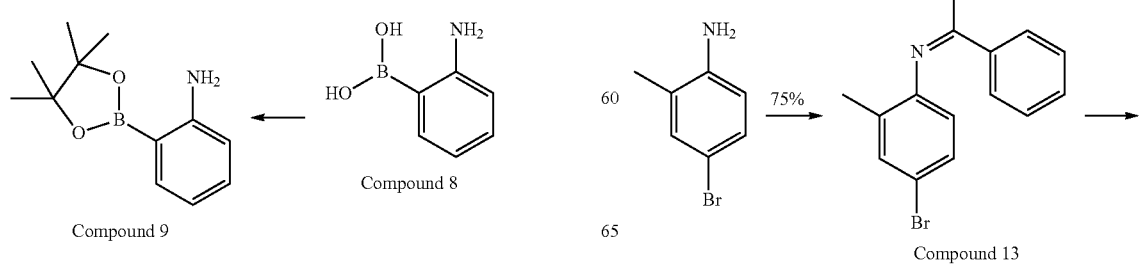

13
-continued
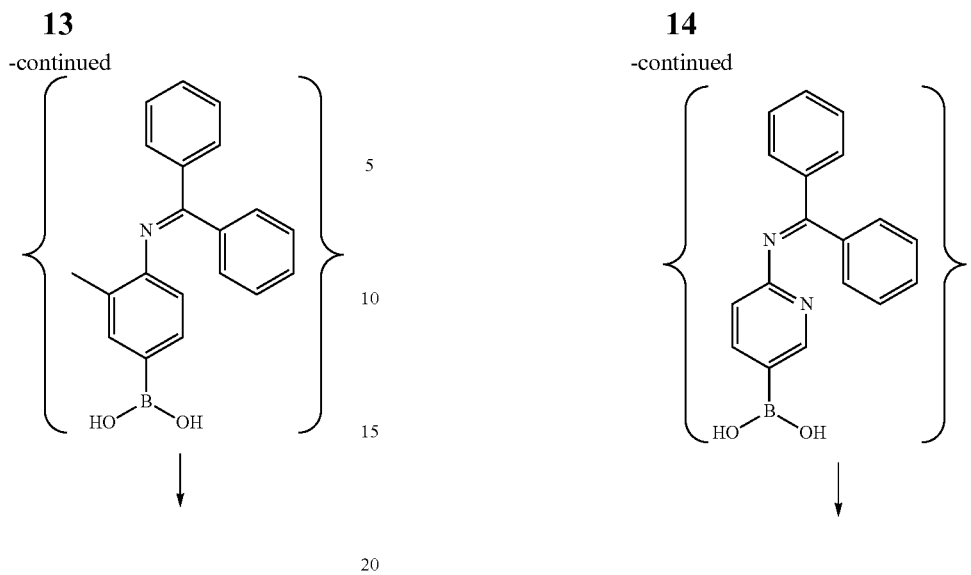
Compound 15
Compound 14
Preparation of 4-amino, 3-methylphenylboronic acid pinacol ester
Example F
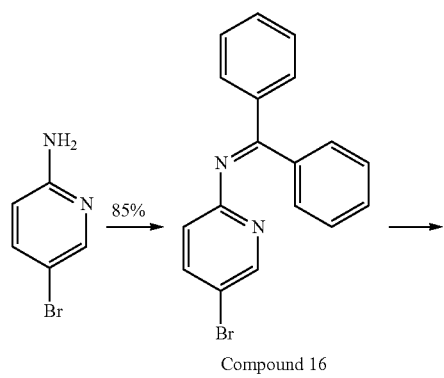
Compound 16
14
-continued
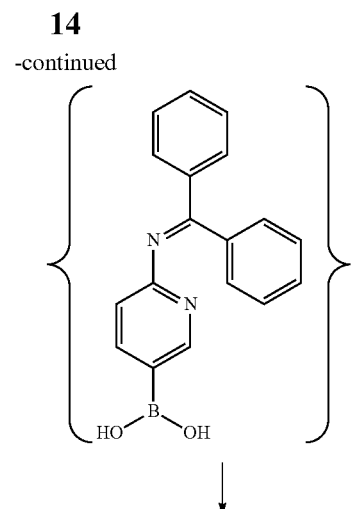
Compound 18
Compound 17
Preparation of 6-amino, 3-pyridinylboronic acid pinacol ester
Example G
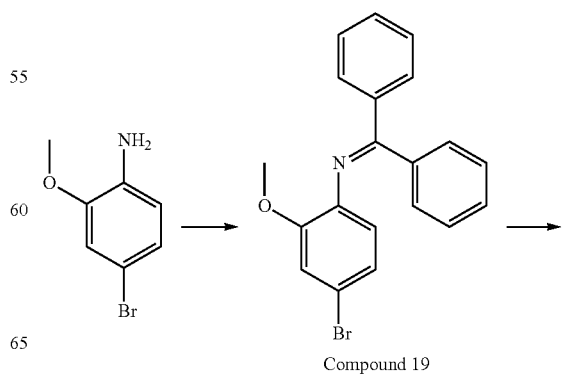
Compound 19

-continued

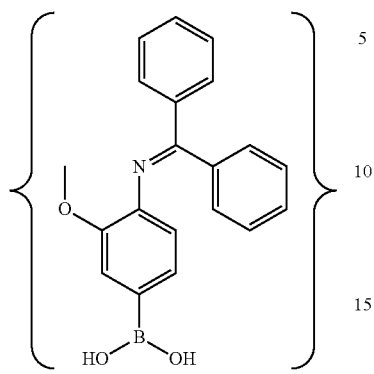

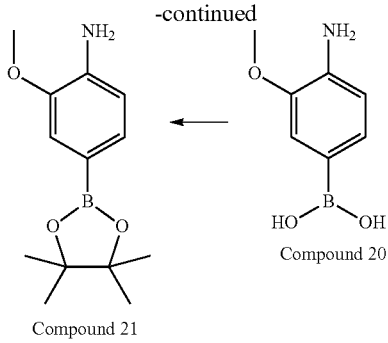

Compound 20

Compound 21

Molecular Weight.: 249,11
m/z: 249.15 (100.0%), 248.16 (24.8%),
250.16 (14.8%), 249.16 (3.6%), 251.16 (1.6%)

Preparation of 4-amino, 3-methoxyphenylboronic acid pinacol ester

TABLE 2

| Compound number | Molecular weight/Mass spectrum | DSC (peak) or mp | NMR/IR |
|---|---|---|---|
| | Chemico-physical properties of compounds 1-6 | | |
| 1 | Molecular Weight: 336.23 Massa spectra: (m/z) 335, 337. | na | na |
| 2 | Molecular Weight: 136.94 Mass spectra ESI/DPI technique positive ionization (m/z): 138 (100%), 137 (23%), 139 (7%) | na | na |
| 3 | Molecular Weight: 219.09 Mass spectra (m/z): 219, 218. | na | na |
| 4 | Molecular Weight: 336.23 Mass spectra (m/z): 335, 337 | 70° C. | 1H-NMR (400 MHz, CDCl3) δ = 6.60 (dq, 1H, 3JHH = 7.8 Hz, 4JHH = 1.7 Hz), 6.91 (t, 1H, 3JHH = 1.7 Hz), 6.97 (t, 1H, 3JHH = 7.8 Hz), 7.04 (dq, 3JHH = 7.8 Hz, 4JHH = 1.7 Hz), 7.09-7.11 (m, 2H), 7.26-7.30 (m, 3H), 7.38-7.41 (m, 2H), 7.45-7.49 (m, 1H), 7.72-7.74 (m, 2H). IR(cm-1): 3466 (w), 3370 (w), 3060 (w), 1656 (m), 1613 (m), 1587 (s), 1561 (s), 1490 (m), 1480 (m), 1465 (s), 1412 (w), 1316 (s), 1294 (s), 1279 (s), 1220 (m), 1143 (m), 1066 (m), 1026 (w), 960 (m), 942 (w), 920 8m), 887 (w), 856 (s), 847 (m), 810 (w), 781 (s), 768 (s), 723 (m), 704 (s), 691 (s), 677 (s), 651 (s), 638 (m), 613 (w) |
| 5 | Molecular Weight: 136.94 Mass spectra ESI/DPI technique positive ionization (m/z): 138 (100%), 137 (23%), 139 (7%) | 131 + 163° C. | 1H-NMR (400 MHz, dmso-d6 + D2O); δ = 6.63 (m, 1H), 6.98 (m, 3H), NH2, B(OH)2 not observed due to H-D exchange; IR(cm-1): 3332 (w), 3220 (w), 3033 (w), 1615 (m), 1602 (m), 1580 (s), 1498 (w), 1443 (m), 1390 (s), 1327 (s), 1295 (s), 1243 (s), 1220 (m), 1143 (m), 1066 (m), 1164 (s), 1105 (m), 1069 (m), 1018 (m), 994 (m), 891 (m), 793 (s), 751 (s), 706 (s) |

TABLE 2-continued

Chemico-physical properties of compounds 1-6

| Compound number | Molecular weight/Mass spectrum | DSC (peak) or mp | NMR/IR |
|---|---|---|---|
| 6 | Molecular Weight: 219.09 Mass spectra (m/z): 219, 218. | 94-96° C. | 1H-NMR (400 MHz, CDCl3); δ = 1.33 (s, 12H), 3.62 (s, 2H), 6.77-6.80 (m, 1H), 7.13-7.22 (m, 3H). IR(cm−1): 3464 (s), 3374 (s), 3232 (w), 2987 (s), 1627 (s), 1601 (m), 1578 (s), 1493 (w), 1441 (s), 1392 (m), 1357 (s), 1320 (s), 1263 (s), 1211 (w), 1220 (m), 1143 (m), 1066 (m), 1169 (m), 1110 (w), 1076 (s), 991 (w), 965 (m), 906 (m), 851 (s), 792 (s), 705 (s) |

TABLE 3

Chemico-physical properties of compounds 7-12

| | | | |
|---|---|---|---|
| 7 | Molecular Weight: 336.23 Mass spectra ESI/DPI technique, positive ionization (m/z): 339 (20%) 338 (100%), 337 (21%) 336 (99%), | 70.9° C. | 1H-NMR (500 MHz, CDCl3) δ = 6.70 (d, 1H, 7.7 HZ), 6.85 (dt, 1H, 7.7 Hz), 7.12 (t, 1H, 8.3 Hz), 7.20 (d, 2H, 7.3 Hz), 7.25-7.40 (m, 3H), 7.40-7.50 (m, 3H), 7.50-7.60 (m, 1H), 7.90 (d, 2H, 7.7 Hz), IR(cm−1): 3052 (w), 3025 (w), 1615 (s), 1596 (m), 1576 (s), 1490 (m), 1459 (m), 1447 (m), 1429 (m), 1317 (s), 1293 (s), 1223 (s), 1178 (m), 1145 (m), 1113 (m), 1073 (w), 1044 (m), 1024 (s), 1002 (m), 957 (m), 935 (w), 916 (w), 829 (m), 786 (s), 770 (s), 760 (s), 694 (s), 675 (s), 667 (s) |
| 8 | Molecular Weight: 136.94 ESI/DPI technique positive ionization (m/z): 138 (100%), 137 (22%), 139 (9%) | 102.1° C. | 1H-NMR (500 MHz, CDCl3); δ = 6.95 (t, 1H, 7.3 Hz), 7.09 (d, 1H, 8.1 Hz), 7.38 (dt, 1H, 7.2 Hz), 7.71 (d, 1H, 7.4 Hz); IR(cm−1): 3487 (m), 3380 (m), 2976 (m), 2936 (w), 1625 (m), 1605 (s), 1567 (m), 1488 (m), 1454 (s), 1387 (m), 1373 (m), 1351 (s), 1310 (s), 1290 (m), 1268 (m), 1245 (s), 1206 (m), 1161 (m), 1135 (s), 1106 (m), 1086 (s), 1055 (m), 1028 (m), 959 (m), 863 (m), 846 (s), 828 (m), 758 (s), 670 (s), 654 (s) |
| 9 | Molecular Weight: 219.09 Mass spectra (m/z): 219, 218. | na | na |
| 10 | Molecular Weight: 370.67 Mass spectra ESI/DPI technique positive ionization (m/z): 372.5 (100%), 373.5 (28%), 374.2 (19%) | 100° C. | 1H-NMR (500 MHz, CDCl3) δ = 6.93 (s, 1H), 7.08 (dd, 1H, 8.4 Hz), 7.12 (d, 1H, 8.4 Hz), 7.20 (d, 2H, 6.9 Hz), 7.28-7.42 (m, 2H), 7.50 (t, 2H, 7.8 Hz), 7.57 (t, 1H, 7.2 Hz), 7.86 (d, 2H, 7.9 Hz), IR(cm−1): 3063 (w), 1671 (w), 1623 (s), 1595 (w), 1570 (s), 1550 (w), 1520 (w), 1486 (w), 1459 (w), 1442 (m), 1415 (w), 1372 (w), 1318 (w), 1298 (w), 1279 (w), 1240 (w), 1224 (w), 1180 (w), 1147 (w), 1131 (w), 1073 (s), 1052 (w), 1029 (w), 999 (w), 953 (s), 919 (m), 870 (m), 861 (s), 800 (s), 789 (m), 771 (m), 738 (m), 725 (w), 695 (vs), 675 (s), 652 (s), 615 (w) |
| 11 | Molecular Weight: 171.39 Mass spectra ESI/DPI technique positive ionization | na | na |

TABLE 3-continued

Chemico-physical properties of compounds 7-12

| | | | |
|---|---|---|---|
| | (m/z): 172 (100%), 174 (20%). | | |
| 12 | Molecular Weight: 253.53 Mass spectra ESI/DPI technique positive ionization (m/z): 253 (26%), 254 (100%), 255 (21%), 256 (33%) | 68° C. | 1H-NMR (400 MHz, dmso-d6) δ = 1.23 (s, 12H), 5.29 (s, 2H), 6.78 (dd, 1H, 3JHH = 7.9 Hz, 4JHH = 1.4 Hz), 7.12-7.14 (m, 2H) IR (cm−1): 3442 ( ), 3350 (m), 2990 (w), 2977 (w), 1627 (w), 1592 (w), 1570 (m), 1492 (w), 1471 (w), 1414 (s), 1391 (m), 1356 (vs), 1323 (m), 1294 (w), 1284 (w), 1273 (w), 1251 (m), 1214 (w), 1164 (w), 1142 (s), 1089 (vs), 1033 (w), 1005 (w), 964 (m), 924 (w), 892 (w), 853 (s), 827 (w), 807 (m), 784 (w), 722 (m), 692 (w), 679 (s), 666 (m) |

TABLE 4

Chemico-physical properties of compounds 13-17

| | | | |
|---|---|---|---|
| 13 | Molecular Weight: 350.25 Mass spectra EST/DPI technique positive ionization (m/z): 350 (99.7%), 351.3 (24%), 252 (100%), 353 (22%) | 156-158° C. | 1H-NMR (400 MHz, CDCl3) δ = 2.15 (s, 3H), 6.28 (d, 1H, 3JHH = 8.3 Hz), 7.00 (dd, 1H, 3JHH = 8.3 Hz, 4JHH = 2.2 Hz), 7.05-7.07 (m, 2H), 7.20-7.21 (m, 1H), 7.23-7.29 (m, 3H), 7.38-7.42 (m, 2H), 7.45-7.49 (m, 1H), 7.75-7.77 (m, 2H); IR (cm−1); 3026 (w), 1692 (w), 1613 (m), 1595 (w), 1570 (m), 1489 (w), 1473 (m), 1444 (w), 1390 (w), 1315 (m), 1304 (w), 1294 (w), 1283 (w), 1269 (w), 1228 (m), 1186 (w), 1149 (w), 1119 (m), 1076 (w), 1029 (w), 1000 (w), 972 (w), 958 (w), 945 (w), 931 (w), 917 (w), 868 (m), 826 (s), 787 (s), 762 (m), 738 (m), 701 (s), 692 (s), 677 (m), 662 (s), 621 (w) |
| 14 | Molecular Weight: 150.97 Mass spectra ESI/DPI technique positive ionization (m/z): 151 (100%), 152 (15%). | na | na |
| 15 | Molecular Weight: 233.11 Mass spectra ESI/DPI technique positive ionization (m/z): 233.5 (24%), 234.4 (100%), 235.4 (13%) | 96-98° C. | 1H-NMR (500 MHz, CDCl3) δ = 1.35 (s, 12H), 2.35 (s, 3H), 7.00 (d, 1H, 7.7 Hz), 7.59 (d, 1H, 7.7 Hz), 7.61 (s, 1H); IR (cm−1): 3480 (w), 3456 (w), 3372 (w), 2978 (m), 2927 (m), 1622 (s), 1604 (w), 1571 (m), 1469 (w), 1458 (w), 1408 (m), 1387 (m), 1379 (m), 1350 (s), 1324 (s), 1302 (s), 1288 (m), 1267 (s), 1210 (w), 1197 (m), 1134 (s), 1109 (w), 1035 (w), 1003 (m), 986 (m), 962 (s), 906 (m), 912 (m), 851 (s), 824 (s), 738 (m), 686 (m), 667 (s) |
| 16 | Molecular Weight: 337.21 Mass spectra ESI/DPI technique positive ionization (m/z): 337.4 (100%), 338.4 (20%), 339.3 (99.5%), 340.3 (20%) | 117-120° C. | 1H-NMR (500 MHz, CDCl3) δ = 6.56 (d, 1H, 8.6 Hz), 7.32-7.42 (m, 4H), 7.42-7.50 (m, 2H), 7.50-7.56 (m, 2H), 7.56-7.70 (m, 2H), 7.85 (d, 1H, 7.5 Hz), 8.40 (d, 1H, 2.0 Hz); IR (cm−1): 3054 (w), 3041 (w), 1629 (s), 1595 (m), 1567 (s), 1546 (m), 1489 (w), 1447 (s), 1397 (w), 1354 (m), 1318 (s), 1291 (s), 1279 (s), 1242 (s), 1221 (m), 1177 (w), 1550 (m), 1124 (s), 1093 (m), 1075 (m), 1027 (w), 1002 (s), 960 (s), |

TABLE 4-continued

Chemico-physical properties of compounds 13-17

|   |   |   |   |
|---|---|---|---|
|   |   |   | 913 (m), 941 (m), 914 (m), 830 (s), 784 (s), 775 (s), 753 (s), 720 (w), 700 (s), 672 (s) |
| 17 | Molecular Weight: 137.93 Mass spectra ESI/DPI technique positive ionization (m/z): 139 (100%), 138 (20%), 140 (5%) | na | na |

TABLE 5

Chemico-physical properties of compounds 18-21

| Compound number | Molecular weight/Mass spectrum | DSC (peak) or mp | NMR |
|---|---|---|---|
| 18 | Molecular Weight: 220.08<br>Mass spectra (m/z): 220, 219. | na | na |
| 19 | Molecular Weight: 366.25<br>Mass spectra ESI/DPI technique positive ionization (m/z): 366.3 (100%), 367.3 (22%), 368.3 (99.9%), 369.3 (21%) | 76.1° C. | 1H-NMR (500 MHz, CDCl3) δ = 3.60 (s, 3H), 6.89 (d, 1H, 1.8 Hz), 6.96 (d, 1H, 7.7 Hz), 7.19 (d, 2H, 7.1 Hz), 7.25-7.35 (m, 3H), 7.35-7.45 (m, 1H), 7.48 (t, 2H, 7.5 Hz), 7.58 (t, 1H, 7.3 Hz), 7.85 (d, 2H, 7.3 Hz);<br>IR (cm−1): 3487 (m), 3381 (m), 2995 (w), 2977 (w), 1623 (m), 1606 (s), 1567 (m), 1487 (m), 1455 (s), 1448 (s), 1389 (s), 1352 (s), 1315 (s), 1292 (m), 1244 (s), 1209 (m), 1177 (w), 1160 (w), 1136 (s), 1120 (m), 1107 (m), 1085 (m), 1056 (s), 1028 (m), 1018 (s), 1001 (s), 958 (m), 928 (s), 911 (s), 861 (m), 851 (m), 829 (s), 813 (s), 796 (s), 781 (s), 759 (m), 742 (s), 710 (s), 688 (m), 671 (m), 655 (m). |
| 20 | Molecular Weight: 166.97<br>Mass spectra (m/z): 167, 166, 168. | na | na |
| 21 | Molecular Weight: 249.11<br>Mass spectra ESI/DPI technique positive ionization (m/z): 249.6 (24%), 250.4 (100%), 251.4 (14.7%) | 106.6 | 1H-NMR (500 MHz, CDCl3) δ = 1.18 (s, 12H), 3.96 (s, 3H), 6.85 (d, 1H, 7.7 Hz), 7.25 (s, 1H), 7.35 (d, 1H, 7.7 Hz);<br>IR (cm−1): 3469 (s), 3366 (s), 3200 (s), 3060 (s), 2999 (s), 2977 (s), 2965 (s), 2940 (s), 1618 (m), 1593 (s), 1575 (s), 1525 (s), 1476 (s), 1464 (s), 1449 (s), 1418 (m), 1394 (s), 1376 (m), 1342 (m), 1302 (m), 1270 (m), 1219 (m), 1178 (s), 1171 (s), 1140 (m), 1108 (s), 1090 (m), 1063 (s), 1031 (m), 1012 (s), 964 (m), 932 (s), 903 (m), 883 (s), 854 (m), 823 (m), 799 (s), 762 (s), 739 (s), 700 (s), 682 (m), 673 (m). |

Comparative Example

Preparation of 3-aminophenylboronic acid pinacol ester According to Example 1 of US2008/0269523A1

A mixture of 38 Kg (221 moles) of 3-bromo aniline, 40 Kg (221 mole) benzophenone and 2.1 kg (0.05 eq) of p-toluenesulfonic acid monohydrate in 120 kg toluene is refluxed for 150 h under reflux, whereby water is azeotropically removed. Eventually obtained solid substance is filtered, the filtrate is free from toluene by distillation. The residue is brought to crystallisation through slow addition of methanol in the cold. The crystals are sucked, washed with toluene and dried under vacuum. The thus prepared solid is the protected amine benzhydryliden-(3-bromo-phenyl)-amine. Yield: 37.5 kg (113 moles, 51%)

472 g (1.4 mole) benzhydryliden-(3-bromo-phenyl)-amine are dissolved in 3.47 kg dry THF and cooled to −78° C. At this temperature 420 g (1.54 moles) of 2.5 M n-butyllithium solution in hexane is slowly added. The mixture is continually stirred for 60 min and then cooled to −85° C. 176 g (1.67 moles) of trimethylborate are slowly added. The mixture is again stirred for 60 min, then left to warm up to −10° C. and then poured into a prepared solution of 229 g of 96% sulphuric acid in 3.14 Kg water covered with a layer of 1.18 Kg of toluene. The mixture is stirred for one hour After completion of phase separation the aqueous phase is covered with a layer of 4.72 Kg of fresh toluene and 199.4 g (1.69 moles) pinacol are added. By adding 1.30 Kg of 10% sodium hydroxide solution a pH-value of about 8.5 is set. The mixture is stirred intensely for 12 h, then again phase separation takes place. From the organic phase the bulk of the solvent is removed at 100-150 mbar. The residue is cooled to −5° C. The thereby obtained solid substance is sucked off, washed and dried under vacuum. Thus, colorless crystals of 3-aminophenylboronic acid pinacol ester are obtained. Yield: 210 g (0.95 moles, 69%). Overall yields: 35%.

The invention claimed is:

1. A process for the preparation of aminoaryl boronic acids and esters thereof of formula (I)

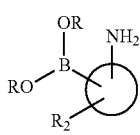

(I)

wherein

represents an aryl group;

$R_2$ is selected from H, Cl, F, $C_1$-$C_3$ alkyl and $C_1$-$C_3$ alkoxy;

R is selected from H, $C_1$-$C_2$ alkyl or, taken together with the other R, forms a ring of formula

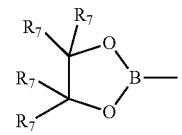

wherein $R_7$ is H or $C_1$-$C_3$ alkyl which process comprises a condensation reaction between a dialkyl ketal derivative of formula (V)

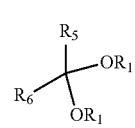

(V)

wherein $R_1$ is a $C_1$-$C_2$ alkyl;
$R_5$ and $R_6$ are aryl;
and a bromo aminoaryl compound of formula (II)

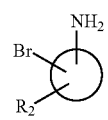

(II)

wherein

and $R_2$ are as defined above,
to yield a corresponding bromo imino derivative of formula (III)

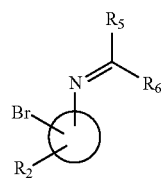

(III)

wherein

$R_2$, $R_5$ and $R_6$ are as defined above.

2. The process according to claim 1, wherein said aryl group is selected from phenyl, biphenyl, and naphthyl.

3. The process according to claim 1, wherein $R_2$ is selected from H, Cl, F, $C_1$-$C_3$ alkyl and $C_1$-$C_3$ alkoxy.

4. The process according to claim 1, wherein said dialkyl ketal derivative of formula (V) is obtained by reaction of a ketone of formula $R_5R_6C$=O with a trialkyl orthoformate of formula $HC(OR_1)_3$ in the presence of an acid catalyst.

5. The process according to claim 4, wherein said ketone is benzophenone and said trialkyl orthoformate is selected from trimethyl orthoformate and triethyl orthoformate.

6. The process according to claim 4, wherein said ketone is used in a concentration between 1.5 mol/l and 3.5 mol/l, and said trialkyl othoformate is used in a molar ratio comprised between 0.5 and 3, with respect to the ketone of formula $R_5R_6C=O$.

7. The process according to claim 4, wherein said ketone of formula $R_5R_6C=O$ is reacted with the trialkyl orthoformate of formula $HC(OR_1)_3$ in an alcoholic solvent of formula $R_1$—OH.

8. The process according to claim 7, wherein said alcoholic solvent of formula $R_1$—OH is mixed with toluene and a volume ratio between said alcoholic solvent and said toluene is between 3 and 2.

9. The process according to claim 7, wherein said ketone of formula $R_5R_6C=O$ is reacted with the trialkyl orthoformate at a temperature between 40° C. and 150° C.

10. The process according to claim 4, wherein a molar ratio between said ketone of formula $R_5R_6C=O$ and said bromo aminoaryl compound of formula (II) is between 0.75 and 2.

11. The process according to claim 1, wherein said condensation reaction between said dialkyl ketal derivative of formula (V) and said bromo aminoaryl compound of formula (II) takes place in an organic solvent selected from tetrahydrofuran, methyltetrahydrofuran, toluene, 1,4-dioxane, diethyleneglycol dimethyl ether hexane, cyclohexane, heptane and mixtures thereof.

12. The process according to claim 1, wherein said condensation reaction is performed at a temperature between 70° C. and 140° C.

13. The process according to claim 1, further comprising a metalation of the bromo imino derivative of formula (III) and conversion with a compound of formula $B(OR')_3$, to yield a corresponding boronic acid derivative of formula (IV)

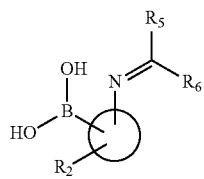

(IV)

wherein

$R_2$, $R_5$ and $R_6$ are as defined above, and R' is a $C_1$-$C_6$ alkyl.

14. The process according to claim 13, wherein said metalation reaction takes place in the presence of an organolithium compound in an aprotic organic solvent selected from saturated and unsaturated hydrocarbons.

15. The process according to claim 14, wherein said organolithium compound is an alkyl lithium, and said organolithium compound is used in a concentration between 0.5 mol/l and 2.5 mol/l.

16. The process according to claim 13, wherein said compound of formula $B(OR')_3$ is trimethyl-, triethyl- or triisopropyl borate, and said compound of formula $B(OR')_3$ is used in a molar ratio comprised between 1.0 and 1.5, with respect to the bromo imino derivative of formula (III).

17. The process according to claim 13, wherein said compound of formula $B(OR')_3$ is reacted for a period of time between 10 minutes and 3 hours at a temperature between −50° C. and −100° C.

18. The process according to claim 13, wherein said compound of formula (IV) is not isolated and is acidified to yield an aminoaryl boronic acid of formula (Ia) or a salt thereof

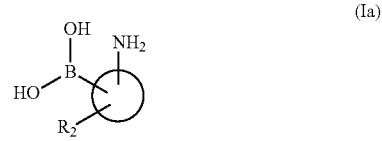

(Ia)

wherein

and $R_2$ are as defined above.

19. The process according to claim 18, further comprising esterification of the aminoaryl boronic acid of formula (Ia) or salt thereof with an alcohol of formula R—OH, wherein R is as defined above, to give the boronic ester of formula (I)

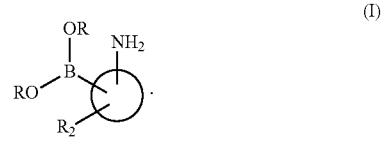

(I)

20. The process according to claim 19, wherein said esterification takes place in a biphasic aqueous/organic solvent mixture.

21. The process according to claim 20, wherein said organic solvent is selected from toluene, xylenes, $C_5$-$C_{10}$ linear or branched hydrocarbons, ethers, and mixtures thereof, and a volume ratio between said aqueous and said organic solvent is between 0.5 and 1.5.

* * * * *